US012564727B2

(12) United States Patent
Carmona Tortolero et al.

(10) Patent No.: US 12,564,727 B2
(45) Date of Patent: Mar. 3, 2026

(54) SYSTEM AND METHOD FOR MULTI-COIL STEERABLE AND SELECTIVELY FOCUSSED TRANSCRANIAL MAGNETIC STIMULATION

(71) Applicant: Virginia Commonwealth University, Richmond, VA (US)

(72) Inventors: Ivan C. Carmona Tortolero, Richmond, VA (US); Ravi L. Hadimani, Richmond, VA (US); Mark S. Baron, Richmond, VA (US); Deepak Kumbhare, Richmond, VA (US)

(73) Assignee: Virginia Commonwealth University, Richmond, VA (US)

( * ) Notice: Subject to any disclaimer, the term of this patent is extended or adjusted under 35 U.S.C. 154(b) by 1054 days.

(21) Appl. No.: 17/577,887

(22) Filed: Jan. 18, 2022

(65) Prior Publication Data

US 2022/0241605 A1     Aug. 4, 2022

Related U.S. Application Data

(60) Provisional application No. 63/137,788, filed on Jan. 15, 2021.

(51) Int. Cl.
  *A61N 2/02*        (2006.01)
  *A61N 2/00*        (2006.01)
(52) U.S. Cl.
  CPC .............. *A61N 2/02* (2013.01); *A61N 2/006* (2013.01)

(58) Field of Classification Search
  CPC .......... A61N 2/00; A61N 2/002; A61N 2/004; A61N 2/006; A61N 2/008; A61N 2/02
  See application file for complete search history.

(56) References Cited

U.S. PATENT DOCUMENTS

2007/0260107 A1* 11/2007 Mishelevich .......... A61N 2/004
                                                          600/14
2010/0286470 A1* 11/2010 Schneider .............. A61N 2/006
                                                          600/14

* cited by examiner

*Primary Examiner* — Carrie R Dorna
(74) *Attorney, Agent, or Firm* — WCF IP

(57) ABSTRACT

An example method includes positioning above the transcranial region, an arrangement of solenoids, and selecting a target zone from among a plurality of zones. A zone-specific set of Q solenoids is identified from the arrangement of solenoids, based on the target zone. The zone-specific set includes a pair of mutually adjacent ones of the solenoids. A Q-element solenoid feed modulation state vector is generated, which defines a Q-current element feed current modulation state. The Q-current element feed current modulation state is configured to cause the zone-specific set of Q solenoids to generate Q individual, spatially configured, time-varying magnetic fields that, in combination, establish a transcranial magnetic stimulation (TMS) inducing time-varying magnetic field, which induces a target hotspot TMS electric field. The hotspot TMS electric field is focalized to the target zone.

20 Claims, 12 Drawing Sheets

| INDIRECT SWITCHED STIMULATION PATTERNS (TIME-AVERAGED) | | | | | | | | | | | | | | | | |
|---|---|---|---|---|---|---|---|---|---|---|---|---|---|---|---|---|
| # | Zone to be Stimulated (target | Average E-field Direction Toward (x) | Coil 1 | | Coil 2 | | Coil 3 | | Coil 4 | | Coil 5 | | Coil 6 | | Coil 0 | |
| | | | T1 | T2 | T1 | T2 | T1 | T2 | T1 | T2 | T1 | T2 | T1 | T2 | T1 | T2 |
| 61 | 0 | ↗(c) | 1 | 0 | -1 | 1 | 0 | -1 | -1 | 0 | 1 | -1 | 0 | 1 | 0 | 0 |
| 62 | 0 | →(e) | 0 | 1 | 1 | 0 | -1 | 1 | 0 | -1 | -1 | 0 | 1 | -1 | 0 | 0 |
| 63 | 0 | ↘(g) | 1 | -1 | 0 | 1 | 1 | 0 | -1 | 1 | 0 | -1 | -1 | 0 | 0 | 0 |
| 64 | 0 | (i)↙ | 1 | 0 | 1 | -1 | 0 | 1 | 1 | 0 | -1 | 1 | 0 | -1 | 0 | 0 |
| 65 | 0 | (k)← | 0 | -1 | -1 | 0 | 1 | -1 | 0 | 1 | 1 | 0 | 1 | 1 | 0 | 0 |
| 66 | 0 | (a)↖ | -1 | 1 | 0 | -1 | -1 | 0 | 1 | -1 | 0 | 1 | 1 | 0 | 0 | 0 |

| DIRECT STIMULATION PATTERNS | | | | | | | | | |
|---|---|---|---|---|---|---|---|---|---|
| # | Zone to be Stimulated (target | E-field Direction | Coil 1 | Coil 2 | Coil 3 | Coil 4 | Coil 5 | Coil 6 | Coil 0 |
| 1 | B | ↑ | 1 | -1 | 0 | 0 | 0 | 0 | 0 |
| 2 | | ↓ | -1 | 1 | 0 | 0 | 0 | 0 | 0 |
| 3 | D | ↗ | 0 | 1 | -1 | 0 | 0 | 0 | 0 |
| 4 | | ↙ | 0 | -1 | 1 | 0 | 0 | 0 | 0 |
| 5 | F | ↘ | 0 | 0 | 1 | -1 | 0 | 0 | 0 |
| 6 | | ↖ | 0 | 0 | -1 | 1 | 0 | 0 | 0 |
| 7 | H | ↓ | 0 | 0 | 0 | 1 | -1 | 0 | 0 |
| 8 | | ↑ | 0 | 0 | 0 | -1 | 1 | 0 | 0 |
| 9 | J | ↙ | 0 | 0 | 0 | 0 | 1 | -1 | 0 |
| 10 | | ↗ | 0 | 0 | 0 | 0 | -1 | 1 | 0 |
| 11 | L | ↖ | -1 | 0 | 0 | 0 | 0 | 1 | 0 |
| 12 | | ↘ | 1 | 0 | 0 | 0 | 0 | -1 | 0 |

| | | | DIRECT STIMULATION PATTERNS | | | | | | |
|---|---|---|---|---|---|---|---|---|---|
| # | Zone to be Stimulated (target | E-field Direction | Coil 1 | Coil 2 | Coil 3 | Coil 4 | Coil 5 | Coil 6 | Coil 0 |
| 13 | a | ↗ | 1 | 0 | 0 | 0 | 0 | 0 | -1 |
| 14 | | ↙ | -1 | 0 | 0 | 0 | 0 | 0 | 1 |
| 15 | c | ↘ | 0 | 1 | 0 | 0 | 0 | 0 | -1 |
| 16 | | ↖ | 0 | -1 | 0 | 0 | 0 | 0 | 1 |
| 17 | e | ↓ | 0 | 0 | 1 | 0 | 0 | 0 | -1 |
| 18 | | ↑ | 0 | 0 | -1 | 0 | 0 | 0 | 1 |
| 19 | g | ↙ | 0 | 0 | 0 | 1 | 0 | 0 | -1 |
| 20 | | ↗ | 0 | 0 | 0 | -1 | 0 | 0 | 1 |
| 21 | i | ↘ | 0 | 0 | 0 | 0 | 1 | 0 | -1 |
| 22 | | ↘ | 0 | 0 | 0 | 0 | -1 | 0 | 1 |
| 23 | k | ↑ | 0 | 0 | 0 | 0 | 0 | 1 | -1 |
| 24 | | ↓ | 0 | 0 | 0 | 0 | 0 | -1 | 1 |

| # | Zone to be Stimulated (target) | E-field Direction | Coil 1 | Coil 2 | Coil 3 | Coil 4 | Coil 5 | Coil 6 | Coil 0 |
|---|---|---|---|---|---|---|---|---|---|
| | | | | | DIRECT STIMULATION PATTERNS (...continuation) | | | | |

| | | | INDIRECT SWITCHED STIMULATION PATTERNS (TIME-AVERAGED) | | | | | | | | | | | | | |
|---|---|---|---|---|---|---|---|---|---|---|---|---|---|---|---|---|
| | Zone to be | E-field | Coil | | Coil | | Coil | | Coil | | Coil | | Coil | | Coil | |
| # | Stimulated | Direction | 1' | 1 | 2' | 2 | 3' | 3 | 4' | 4 | 5' | 5 | 6' | 6 | 0 | 0 |
| | (target | | T1 | T2 | T1 | T2 | T1 | T2 | T1 | T2 | T1 | T2 | T1 | T2 | T1 | T2 |
| 67 | A | ↗ | 1 | 0 | 0 | 0 | 0 | 0 | 0 | 0 | 0 | 0 | 0 | 0 | -1 | 1 |
| 68 | | ↙ | -1 | 0 | 0 | 0 | 0 | 0 | 0 | 0 | 0 | 0 | 0 | 0 | 1 | -1 |
| 69 | C | ↘ | 0 | 0 | 1 | 0 | 0 | 0 | 0 | 0 | 0 | 0 | 0 | 0 | -1 | 1 |
| 70 | | ↖ | 0 | 0 | -1 | 0 | 0 | 0 | 0 | 0 | 0 | 0 | 0 | 0 | 1 | -1 |
| 71 | E | ↓ | 0 | 0 | 0 | 0 | 1 | 0 | 0 | 0 | 0 | 0 | 0 | 0 | -1 | 1 |
| 72 | | ↑ | 0 | 0 | 0 | 0 | -1 | 0 | 0 | 0 | 0 | 0 | 0 | 0 | 1 | -1 |
| 73 | G | ↙ | 0 | 0 | 0 | 0 | 0 | 0 | 1 | 0 | 0 | 0 | 0 | 0 | -1 | 1 |
| 74 | | ↗ | 0 | 0 | 0 | 0 | 0 | 0 | -1 | 0 | 0 | 0 | 0 | 0 | 1 | -1 |
| 75 | I | ↖ | 0 | 0 | 0 | 0 | 0 | 0 | 0 | 0 | 1 | -1 | 0 | 0 | -1 | 1 |
| 76 | | ↘ | 0 | 0 | 0 | 0 | 0 | 0 | 0 | 0 | -1 | 1 | 0 | 0 | 1 | -1 |
| 77 | K | ↑ | 0 | 0 | 0 | 0 | 0 | 0 | 0 | 0 | 0 | 0 | 1 | -1 | -1 | 1 |
| 78 | | ↓ | 0 | 0 | 0 | 0 | 0 | 0 | 0 | 0 | 0 | 0 | -1 | 1 | 1 | -1 |

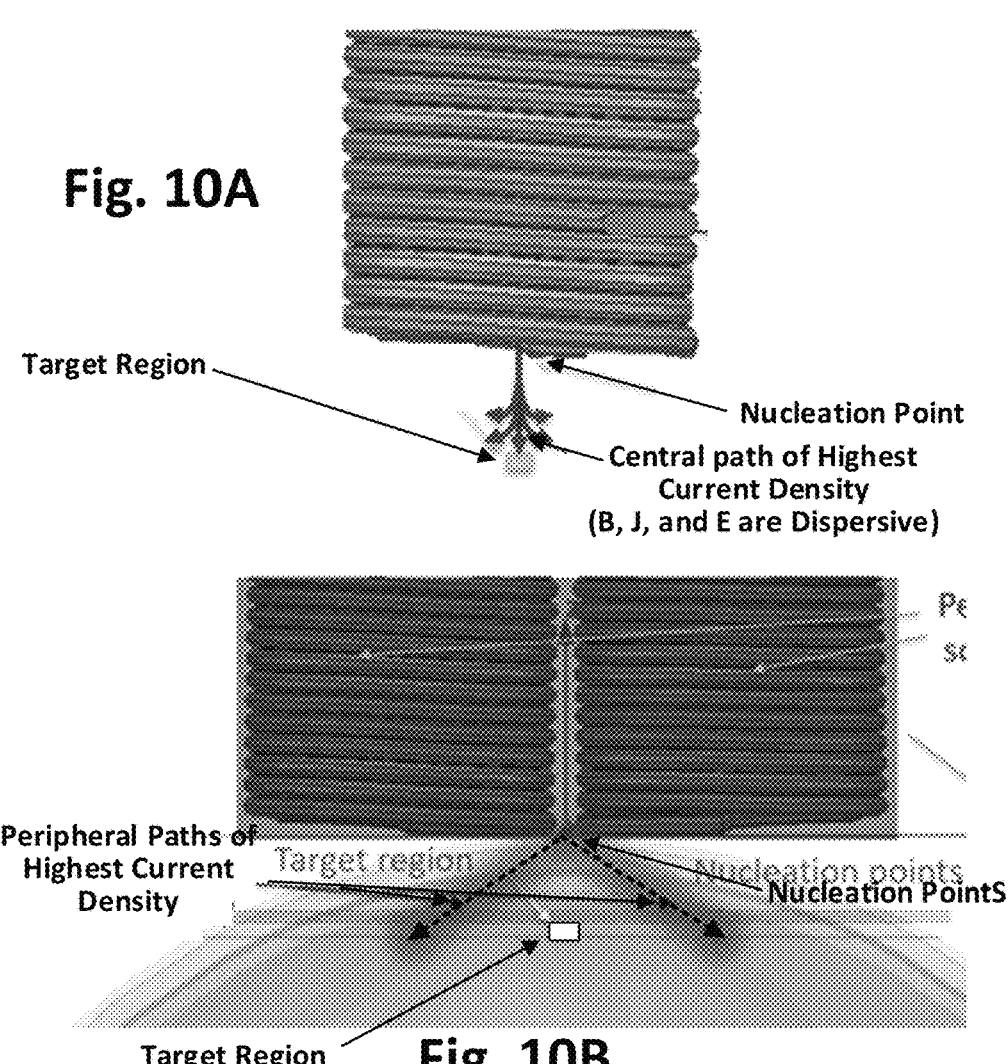

Fig. 10A

Target Region

Nucleation Point

Central path of Highest
Current Density
(B, J, and E are Dispersive)

Pe

Se

Peripheral Paths of
Highest Current
Density

Target region

Nucleation points

Nucleation PointS

Target Region          Fig. 10B

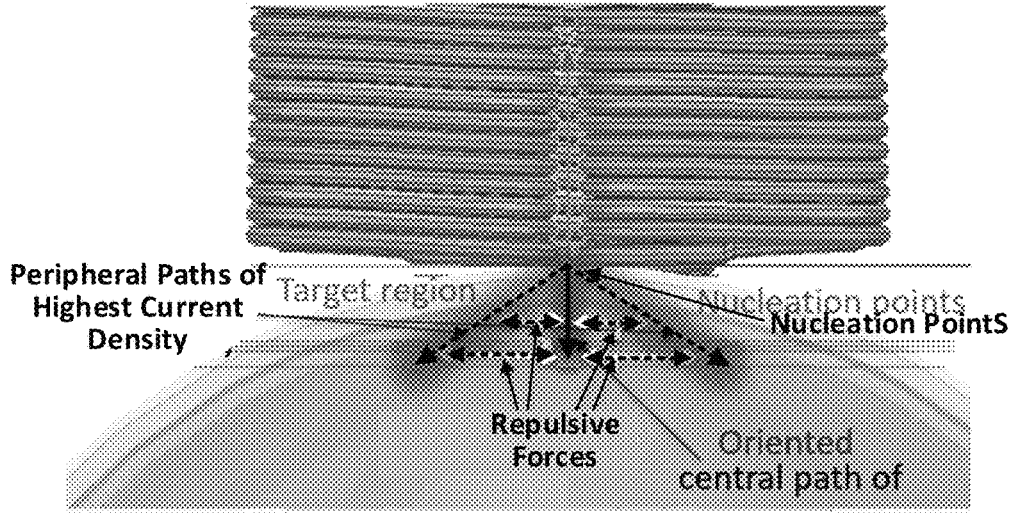

Peripheral Paths of
Highest Current
Density

Target region

Nucleation points

Nucleation PointS

Repulsive
Forces

Oriented
central path of

Fig. 10C

SYSTEM AND METHOD FOR MULTI-COIL STEERABLE AND SELECTIVELY FOCUSSED TRANSCRANIAL MAGNETIC STIMULATION

CROSS-REFERENCE TO RELATED APPLICATIONS

This application claims the benefit of U.S. Provisional Patent Application No. 63/137,788, filed Jan. 15, 2021, which is hereby incorporated by reference in its entirety.

TECHNICAL FIELD

Embodiments generally relate to magnetic field generation in transcranial magnetic stimulation.

BACKGROUND

Transcranial magnetic stimulation (TMS) is a non-invasive neuromodulation technique in which time-varying magnetic fields produced by TMS coils positioned outside a subject's head induce an electric field (E-field) within the subject's brain. The E-field can induce certain changes in synaptic activity of neurons in the subject's brain, e.g., neural firing rates and patterns. Applications include studies of brains, both human and animal, and treatments directed to various neurological and psychiatric disorders, by stimulation strategy toward inducing changes that can improve functionality of connecting regions.

There are technical shortcomings, though, in current TMS techniques. One is that establishing magnetic field strength within a target region sufficient to obtain desired results can produce unwanted stimulation of neurons in regions adjacent the target. This can, for example, limit the accuracy in identifying connections of single specific regions, and of investigating projections in deeper regions.

In current TMS techniques, control of focality and penetration depth can be difficult, as these can depend on multiple variables, including relative positions of coil target relative position, electromagnetic properties of the core materials and tissues, and stimulation parameters (e.g., voltages, currents, frequencies, and waveforms). In addition, an optimal set-up depends on the accurate location of the coil with the appropriate angle. Attaining this set-up can depend on both the ability of the operator and the available instrumentation for stereotactic localization.

TMS coils also do not take into consideration the behavior of the charges inside the target to control the E-field, but just offer a fixed and rigid E-field, which can be consequence of the geometry and not the method.

SUMMARY

Various embodiments address and provide solutions for the above-identified problems.

According to one or more embodiments, an example method provides a selectively focusable and steerable electric field within a transcranial region, and steps can include a positioning, above a transcranial region, an arrangement of solenoids; and selectively establishing, in response to a zone selection data that identifies a target zone, selectable from among a plurality of zones. Steps in the example can also include identifying, based on the target zone data, a zone-specific set of Q solenoids that are from among the arrangement of solenoids, and include at least one pair of mutually adjacent ones of the solenoids. Steps can further include generating a Q-element solenoid feed modulation state vector that defines a Q-current element feed current modulation state, configured to cause the zone-specific set of Q solenoids to generate a corresponding Q individual, spatially configured, time-varying magnetic fields that, in combination, establish a transcranial magnetic stimulation (TMS) inducing time-varying magnetic field focalized to the target region and feeding solenoid feed currents to the zone-specific set of Q solenoids.

Also, according to various embodiments, another example method provides a method for establishing and actively constraining a moving electrical charge flow through a biological tissue, along a flow path that extends in a depth direction aligned with a target region that is spaced from a surface of the biological tissue in a depth direction. Example steps can include nucleating central region electrical charges in the tissue, within a central region above and aligned with the target region, and can include urging the central region electrical charges into a central electrical charge flow, having a mean aligned and parallel to the flow path, by operations including applying a central electrical field of nucleation inducing magnitude. According to one or embodiments, example steps can also include stablishing a plurality of repulsive forces, each urging against the central region electrical charges in the central region electrical charge flow, each being in a direction inward from a respective peripheral location, toward and normal to the flow path.

This Summary identifies example features and aspects and is not an exclusive or exhaustive description of disclosed subject matter. Whether features or aspects are included in or omitted from this Summary is not intended as indicative of relative importance of such features or aspects. Additional features are described, explicitly and implicitly, as will be understood by persons of skill in the pertinent arts upon reading the following detailed description and viewing the drawings, which form a part thereof.

BRIEF DESCRIPTION OF THE DRAWINGS

FIG. 9A shows a perspective view of an example quintuple solenoid arrangement for multi-solenoid selective focused TMS systems and methods in accordance with one or more embodiments; and FIG. 9B top projection view of structure of the FIG. 9A quintuple solenoid arrangement, viewed from FIG. 9A projection 9B-9B.

FIG. 10A shown an annotated front projection of an operation of the central solenoid, aligned above a target region, and corresponding dispersion and migration of induced charges, assuming removal, for purposes of illustration, of peripheral electric fields in accordance various embodiments; FIG. 10B shows paths of peripheral solenoid induced nucleation; and FIG. 10C shows confinement of the central solenoid induced charges by the peripheral solenoid charges, in a process of oriented control of the electric field based on the directional vector of highest current density in accordance with various embodiments.

DETAILED DESCRIPTION

Figures 1A, 1B, 1C:
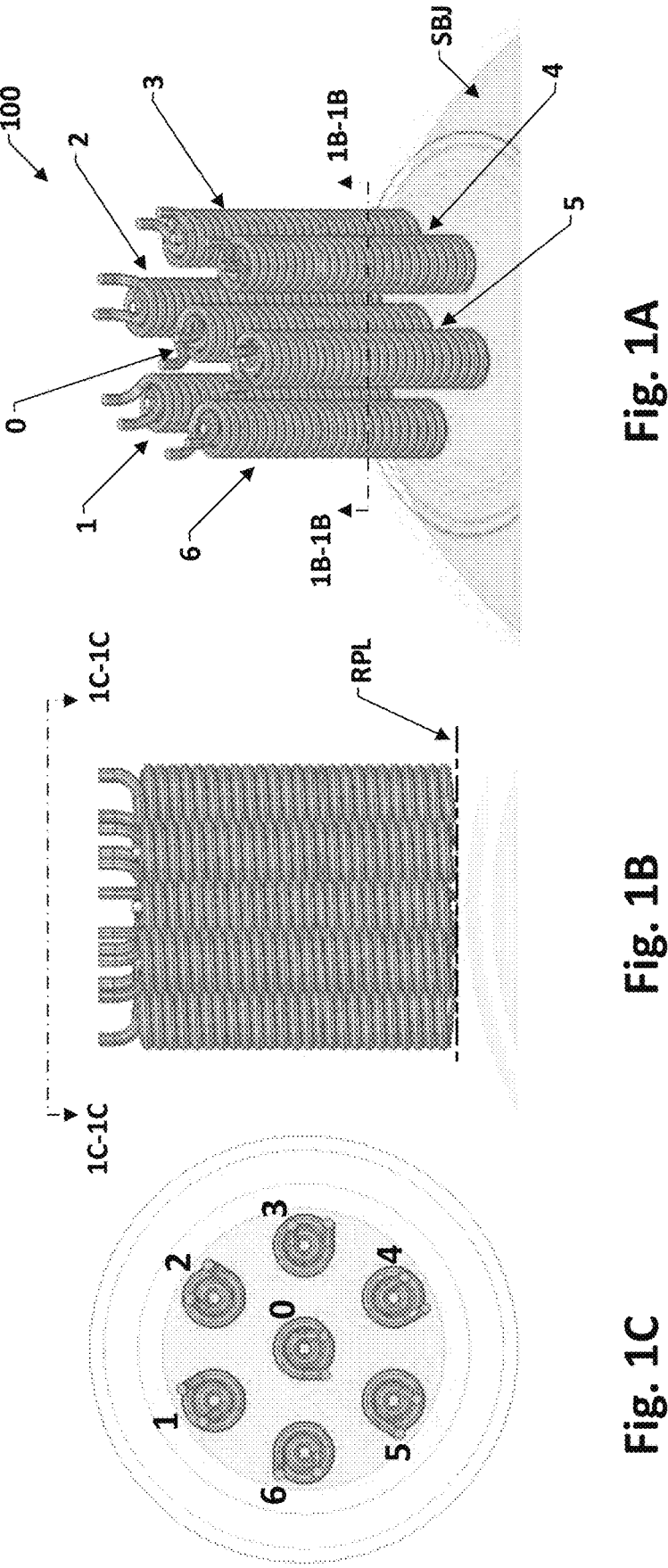
FIG. 1A is a top view of one example configuration of a central solenoid, six peripheral dual-coil solenoid arrangement above a subject, for various methods Space-Varying E-field Vector Modulation (SVEVM) steerable, selectively focused transcranial magnetic stimulation (TMS) according to one or more embodiments.
FIG. 1B is a front projection of the FIG. 1A arrangement.
FIG. 1C is a perspective view of the FIG. 1A arrangement.

Embodiments include an arrangement of solenoids that can be connected to a dynamically configurable, multiple solenoid current feed. The multiple solenoid current feed, in one or more embodiments, is switchable between providing individually modulated solenoid feed current for all the solenoids or for subsets and groups of the solenoids. The individually modulated solenoid feed currents, in combination with the arrangement of solenoids can provide, among other features, an easily repositioned high focality maximum E-field. This can provide, for example, readily selectable positioning and easily repositioning of stimulation inducing hotspots.

Embodiments also include electronic setting of spatial configuration, and such setting can be across a large range of configurations. In various embodiments, features providing such setting and dynamic adjustment of spatial configuration novel concurrent current feeding of sub-groups of the solenoids. Embodiments also include temporal sequencing of the individual solenoid feed currents, and, in an aspect, this includes sequencing that can include concurrent, dynamically adjustable, individual modulation of the current feeds. These features can further provide, for example and without limitation, low complexity, readily placeable, dynamically adjustable averaging. Still further features can include, but are not limited to, additional focality, and tighter granularity in the placement of and in the spatial configuration of the maximum E-field.

According to one or more embodiments, the arrangement of solenoids can be a novel configuration that, for purposes of convenient referencing in this disclosure, will be referred to as a Figure-of-Flower Coil (FFC) arrangement, or "FFC." It will be understood that "Figure-of-Flower Coil" and "FFC," as used in this disclosure, are coined labels that do not have and do not import any intrinsic meaning. In other words, replacing every instance of "Figure-of-Flower Coil" and "FFC" with another coined or arbitrary label will effect no change in the information content of this disclosure or to the scope of the appended claims.

In one or more embodiments, implementation according to the FFC can include a central solenoid and six peripheral solenoids. For purposes of description the central solenoid is alternatively referred to as the "body," and the six peripheral solenoids as "petals." In various embodiments the solenoids can be configured with two winding layers, both being wound around independent round cross-section cores. The core material can be, for example, AISI 1010. The dual winding layers, alone and in combination with the AISI 1010 core material, can provide a higher controllability of the E-field, as described in more detail in later sections of this disclosure. Features and benefits of the higher controllability can include, but are not limited to, increased applicability to humans.

Methods according to various embodiments include what can be a fixed configuration, e.g., the FEC, of solenoids. The configuration and arrangement of the solenoids can establish a coverage area over a target plane and can define, within the coverage area, a plurality of regions or "zones." Each of the zones can be associated with a corresponding sub-plurality of the solenoids. In an aspect, the corresponding sub-plurality of the solenoids can be a group that, when respectively fed appropriately configured sequences of feed currents, will establish a corresponding plurality of time-varying, spatially configured magnetic fields, which can be defined as magnetic flux densities (B-fields). The time-varying, spatially configured magnetic flux densities can have constructive and destructive interferences. These interferences can produce cold and hot spots in the E-field magnitude distribution. By selection of solenoids, and of corresponding feed currents, e.g., modulation of the feed currents, to the selected solenoids, respective locations, intensities, and spatial configurations of the individual magnetic flux densities can be selected, and subsequently adjusted or switched. The adjustment or switching can provide a selectively movable, selectively configurable E-field.

FIG. 1A is a perspective view of one example configuration of a central solenoid, six peripheral dual-coil solenoid arrangement 100 above a subject SBJ, for various methods of Space-Varying E-field Vector Modulation (SVEVM) steerable, selectively focused TMS according to one or more embodiments. FIG. 1B is a front projection of the FIG. 1A arrangement 100 from FIG. 1A projection 1B-1B. FIG. 1C is a top of the arrangement 100 from FIG. 1B top projection 1C-1C.

For TMS application, an example of a functional hotspot E-field strength can include, but is not limited to, 100 volts per meter (V/m). B-field strengths sufficient to induce E-fields of such strength in the described zones can be obtained using, for example, and without limitation, ferromagnetic cores of AISI 1010m which can provide increased flux density in a smaller area. In addition, solenoid current modulation frequencies of, for example and without limitation, 110 kilohertz (KHz) can provide dB/dt values more than 30 times higher than provided by the much lower typical commercial TMS modulation frequencies, e.g., 3 KHz. Features according to various embodiments include, for example and without limitation, reduction in solenoid coil size, for example and not limited to 20:1, compared to other TMS techniques. As illustration, in implementations such as shown, in whole or in part, by examples such as FIGS. 1A through 8B, solenoid coil diameters such as 5 mm, but not limited from being less than or greater than 5 mm, are practical. For purposes of perspective, coil diameters in typical commercially available TMS equipment can be in ranges such as 100 mm.

Figures 2A, 2B:
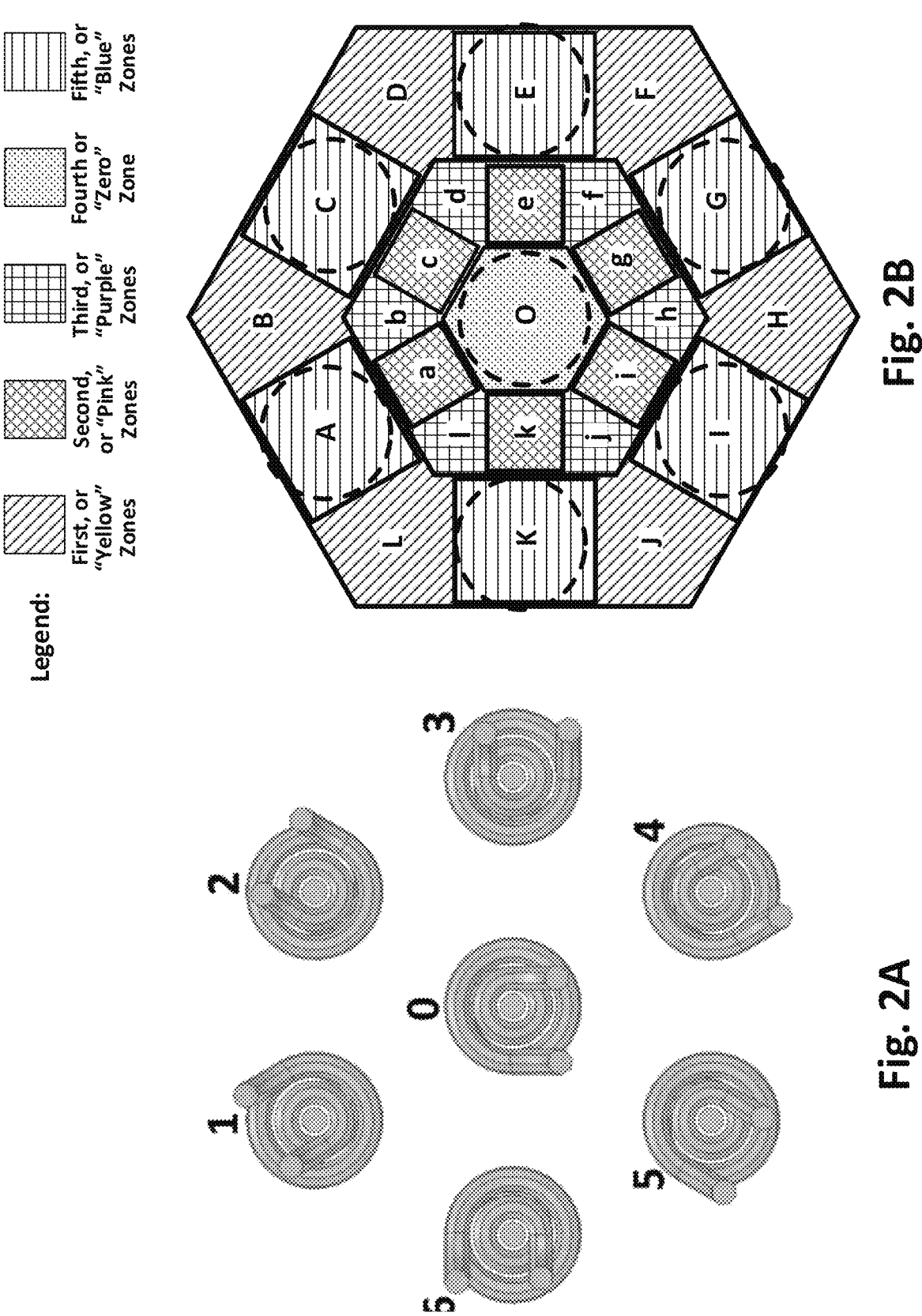
FIG. 2A shows an extraction of the FIG. 1A example configuration the central solenoid, six peripheral dual-coil solenoid arrangement.
FIG. 2B shows a labeled zone mapping of a multi-zone configuration, superposed on the FIG. 1A top view.

FIG. 2A shows a diagram of the FIG. 1C spatial arrangement of the central solenoid 0 and six peripheral dual-coil solenoids 1, 2, 3, 4, 5, and 6. FIG. 2B shows a labeled zone map of a multi-zone configuration, superposed on the FIG. 1C top view. The zone names and labels are arbitrary and are only for purposes of consistent referencing within this disclosure. Persons of ordinary skill, upon reading this disclosure in its entirety will understand that other naming and labeling schemes can be applied. As used in this disclosure, "zone" and "stimulation zone" are synonymous and interchangeable.

Referring to FIG. 2B, and described in more detail in the paragraphs below, the stimulation zones are separated into five (5) diverse groups. As will be understood further by persons of ordinary skill upon reading this discourse in its entirety, the zones are grouped according to the type of polarization that can be applied to the solenoids whose positions define the zone to establish, in the zone, a focalized hotspot TMS electric field. This will be further understood by description in paragraphs below, which reference appended figures showing example polarizations that can be applied to the different types of zones.

One of the groups consists of one zone, which is the zone aligned with the central solenoid 0, and which is of a type unto itself. The central solenoid zone, for purposes of this disclosure, is assigned the name "central zone 0," and is labeled accordingly on FIG. 2B. Also, for purposes of this disclosure, e.g., for convenient referencing of figures' exemplary solenoid feed current modulation vector tables, the 0 zone is alternatively referred to as a "yellow" zone.

Figures 3A, 3B:
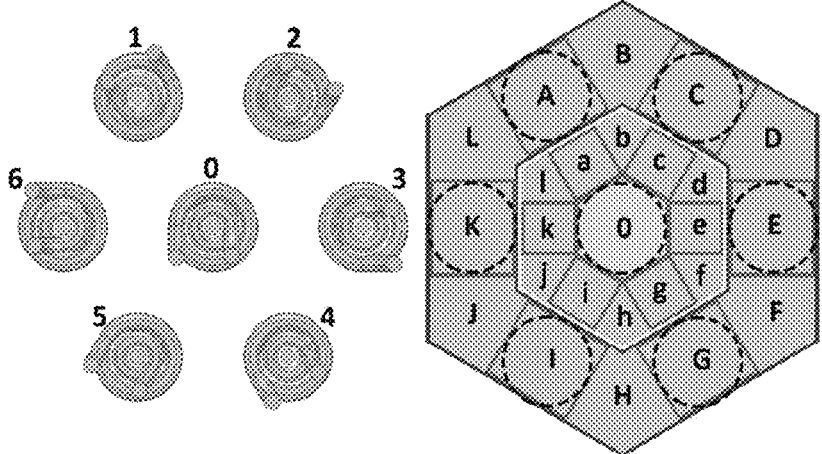
FIG. 3A shows the FIG. 2A solenoid location diagram adjacent another highlighted FIG. 2B zone map, for another type of subject zones.
FIG. 3B shows an example table of six (6) different SVEVM solenoid current modulation state vectors that can be fed to each subject zone's defining solenoids, for selection and selective setting of the direction of the subject zone's hotspot electric field.

Features for selective establishment and control, e.g., adjusting and switching field directions, of high focality TMS inducing E-field hotspots, aligned with and within the boundaries of the 0 zone, are described in reference to FIGS. 3A and 3B.

FIG. 3A shows the FIG. 2A solenoid arrangement diagram adjacent a highlighted "zero" or center zone version of the FIG. 2B zone mapping. In operations establishing a hotspot TMS inducing E-field in the central or 0 zone, individually modulated solenoid currents are fed to all seven of the solenoids, i.e., to the central solenoid 0, the first solenoid 1, second solenoid 2, third solenoid 3, fourth solenoid 4, fifth solenoid 5, and sixth solenoid 6. Each row of the FIG. 3B table spans ten (10) columns. The FIG. 3B table will be described with added detail as it is representative with respect to form and organization of the comparable FIG. 4B table for green zones.

Referring to FIG. 3B, the leftmost column of each row recites a field number, which is an arbitrarily assigned number used for purposes of description as a unique identifier, to a granularity of zone identification, E-field direction, and solenoid feed current modulation values of each TMS inducing hotspot E-field that can be established within the zones defined by this example configuration of "Coil 1," Coil 2," "Coil 3," "Coil 4," "Coil 5," "Coil 6," and "Coil 0."

The next column, in left-to-right order, identifies the "Zone to be Targeted," which for all rows in the FIG. 3B table is the central zone 0.

The rightmost seven columns, namely, "Coil 1," Coil 2," "Coil 3," "Coil 4," "Coil 5," "Coil 6," and "Coil 0, each have value in their first (T1) sub-column and a values in their second (T2) sub-column subintervals each of the coil columns. For this configuration, the defined modulation values consist of three discrete values, which are: "1," "−1" and "0." The value "1" represents, for example, an ON state at a positive phase modulation, e.g., a full ON reference phase oscillating solenoid feed current at the above-identified example 30 KHz oscillation frequency. The value "−1" represents a negative phase modulation, i.e., opposite of the positive phase modulation, e.g., phase shifted by 180 degrees. The "0" value represents an OFF state. of modulation values, for this example configuration, consists of three which are labeled modulation value of the respective coils' feed current during a first sub-interval T1 of a longer interval T1+T2 first duration of longer.

The next column identifies "Average E-field Direction Toward (x)," where "x" is the zone to which the E-field direction points. As seen in FIG. 3B the solenoid current modulation values can be selected. The direction values are represented as graphical arrows. FIG. 3B defines the first (T1) and second (T2) time subintervals for each of the coil columns, which are labeled modulation value of the respective coils' feed current during a first sub-interval T1 of a longer interval T1+T2 first duration of longer corresponds to a seven element embodiment. Example current solenoid current vectors that, in accordance with disclosed embodiments, can be fed to solenoids defining the alignment location of each zone in each of the four among the five groups referenced above will now be described in more detail, referencing in turn FIGS. 3A-3B, 4A-4B, 5A-5B, and 6A-6B. For purposes of description, the SVEVM current modulation state vector will be described as solenoid modulation state vector {CM1, CM2, CM3, CM4, CM5, CM6, CM0}. Fields will be generically referenced as "CMx."

Generation of the Q element modulation state vector can be performed, for example, by an appropriately configured computing device, such as the example described later in reference to FIGS. 12, coupled for example to an external command-controllable Q-output modulated current supply. The external command-controllable Q-output modulated current supply can be, for example and without limitation, local to the solenoids. The external command-controllable Q-output modulated current supply can be coupled to the computing device, for example, by various types and implementation of connection, e.g., by a serial connection. The computing device can include a digital processor device, e.g., an arithmetic logic unit (ALU) coupled to an instruction memory that can store assemblies of instructions from a native instruction set that, when executed by the digital processor device, cause the device to perform in accordance with described processes and operations, function.

According to an embodiment, a high focality E-field hotspot can be placed in the zero zone, i.e., directly under the zero or central solenoid 0, by applying a particular two sub-interval modulation to the solenoid coils. In overview, the first sub-interval modulation feeds a first phase. A fifth scenario was evaluated for the stimulation of the zone "0", with the polarization of the coils 6 and 3 with 5 kA and –5 kA, respectively. To reduce the overstimulation of unwanted zones the same pattern can be combined with a pattern rotated 60 degrees counterclockwise, with the polarization of the correspondent petals for it. This finally produced a pattern with the maximum directly below the central solenoid.

Example current solenoid current vectors that, in accordance with disclosed embodiments, can be fed to solenoids defining the alignment location of each zone in other groups will now be described in more detail, referencing in turn FIGS. 4A-4B, 5A-5B, and 6A-6B.

Figures 4A, 4B:
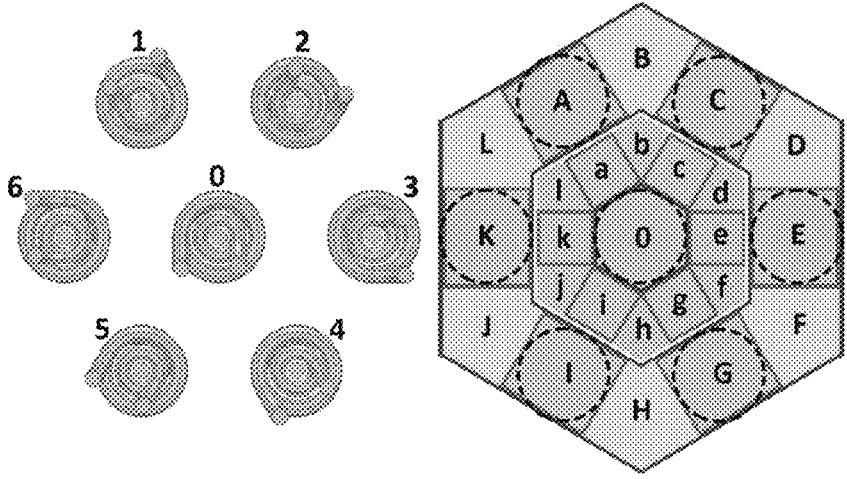
FIG. 4A shows the FIG. 2A solenoid location diagram adjacent a highlighted version of the FIG. 2B zone map, highlighting subject zones.
FIG. 4B shows a table of solenoid feed current modulation state vectors that can be applied to each green zone's respective defining solenoids to establish a desired hotpot electric field, in a selectable one of two directions.

FIG. 4A shows the FIG. 2A solenoid location diagram adjacent a version of the FIG. 2B zone map that highlights "green" zones. For brevity, the "green zones," and "pink zones" that are described in more detail in later paragraphs of this disclosure, herein, can be alternatively referred to as "inter-solenoid" zones. Also, electric fields established in these inter-solenoid zones, through practices in accordance with various disclosed embodiments as described in more detail in later section of this disclosure, can be alternatively referred to as "inter-solenoid electric field(s)." Continuing the above-described FIG. 2A solenoid labeling, and FIG. 2B zone and zone group naming scheme, the green zones are "capital b" (graphically represented as "B"); "capital d" (graphically represented as "D"); "capital f" (graphically represented as "F"); "capital h" (graphically represented as "H"); "capital j" (graphically represented as "J"); and "capital l" (graphically represented as "L"). FIG. 4B shows a table of solenoid feed current modulation state vectors that can be applied to each green zone's respective defining solenoids to establish a desired hotpot electric field. As can be seen in FIG. 4B, the direction can be selectable between two directions.

As visible on FIG. 2B, each of the green zones, being "inter-solenoid zones" as noted above, is centered midway between a particular two consecutive, i.e., adjacent, ones of the peripheral solenoids 1, 2, 3, 4, 5, and 6. The value of "Q" for the zone-specific set of solenoids for each of the green zones is therefore integer 2, and the set consists of said two peripheral solenoids. Stated with reference to the FIG. 4A arrangement and labeling scheme, the zone-specific set of Q solenoids for green zone B is the set of two consecutive peripheral solenoids 1 and 2, i.e., the "first peripheral solenoid 1" and "second peripheral solenoid 2." The zone-specific set of Q solenoids for green zone D is the set of two consecutive peripheral solenoids 2 and 3, i.e., "second peripheral solenoid 2" and "third peripheral solenoid 3"; the zone-specific set of Q solenoids for green zone F is the set of two consecutive peripheral solenoids 3 and 4, i.e., "third peripheral solenoid 3" and "fourth peripheral solenoid 4"; the zone-specific set of Q solenoids for green zone H is the set of two consecutive peripheral solenoids 4 and 5, i.e., "fourth peripheral solenoid 4" and "fifth peripheral solenoid 5," and for green zone J the consists of two consecutive peripheral solenoids 5 and 6, i.e., the "fifth peripheral solenoid 5" and "sixth peripheral solenoid 6," and for green zone L the set is two consecutive peripheral solenoids 6 and 1, i.e., the "sixth peripheral solenoid 6" and "first peripheral solenoid 1."

As shown in FIG. 4B, there can be a selection, which can be automatically or manually performed, between two different directions of the electrical field. The two different directions can be respectively provided by two different SVEVM solenoid modulation state vectors. As will be understood from examples, there is a pattern to a correspondence between modulation phases and the electric field directions. Referring to FIG. 4B, the zone-specific set of solenoids for green zone B are the consecutive first peripheral solenoid 1 and second peripheral solenoid 2. As shown in FIG. 4B table, line #1, to establish a TMS electric field hotspot in green zone B, in a first direction (appearing as an upward pointing vertical field vector on the plane of FIG. 4B) the Q-element solenoid feed modulation state vector comprises a positive modulation feed current (shows as 1) to the first peripheral solenoid 1 and a negative modulation feed current (shown as –1) to the second peripheral solenoid 2. Expressed in terms of the SVEVM solenoid feed modulation state vector, {CM1, CM2, CM3, CM4, CM5, CM6, CM0}, the Q-element solenoid feed modulation state vector at line #1 is {1, –1, 0, 0, 0, 0, 0}. As visible in the FIG. 4B table at lines #2, feeding opposite polarization feed currents, i.e., negative modulation feed current to the first peripheral solenoid 1 and positive modulation feed current to the second peripheral solenoid 2 reverses the hotspot electric field direction. Q-element solenoid feed modulation state vector at line #2 is therefore a reversal of line #1: {–1, 1, 0, 0, 0, 0, 0}.

As can be seen from FIG. 4B line #3 through line #12, the above example establishment of a selectable direction electric field hotspot in green zone B can likewise establish the hotspot electric field in any of the remaining green zones D, F H, J, and L.

Figures 5A, 5B:
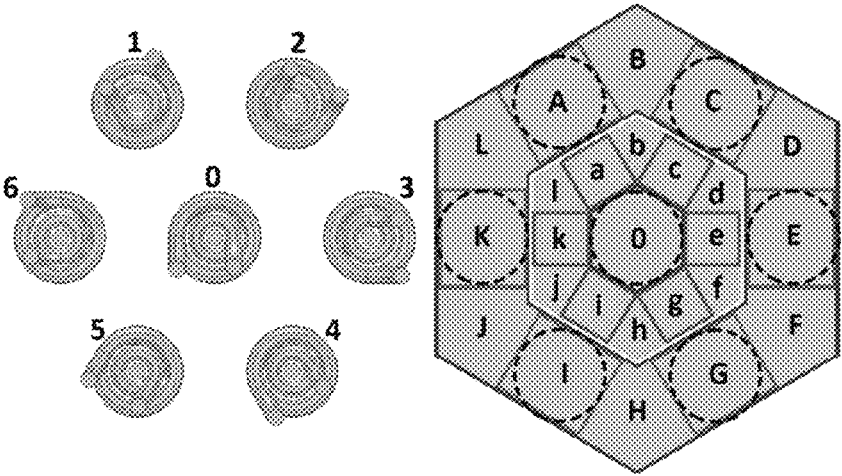
FIG. 5A shows the FIG. 2A solenoid location diagram adjacent a zone map highlighting subject zones.
FIG. 5B shows an example table of two different SVEVM solenoid current modulation state vectors that can be fed to each subject zone's defining solenoids.

FIG. 5A shows a solenoid location diagram adjacent a zone map highlighting "pink" zones. FIG. 5B shows an example table of two different SVEVM solenoid modulation state vectors that can be fed to each pink zone's defining solenoids, for SVEVM placement of an electric field hotspot in the zone. As visible in the figures the pink zones can be verbally referenced as "lower case a;" "lower case c;" "lower case e;" "lower case g;" "lower case i;" and "lower case k." These are graphically represented on FIGS. 5A and 5B as, respectively, a, c, e, g, i, and k. Each of the pink zones is centered midway between the central solenoid and a particular one of the six peripheral solenoids 1, 2, 3, 4, 5, and 6. The six pink zones, a, c, e, g, i, and k, can also be referred "inter-solenoid" zones a, c, e, g, i, and k, as described above for the green zones B, D, F, H, J, and L. In accordance with one or more embodiments, hotspots can be established in any of the pink zones by feeding opposite phase currents to the central solenoid 0 and the zone's corresponding one of the peripheral solenoids. The direction of the hotspot electric field, as visible in the FIG. 5B table, can be selected between two directions by selecting whether the central solenoid is fed the positive phase modulation and the peripheral solenoid the negative phase, or vice versa.

The pink zones, continuing with the example solenoid and zone naming scheme, are zones a, c, e, g, i, and k. Referring to FIG. 5B, arbitrarily selected pink zone c will be used as a representative example. Line #15 and #16 show that feeding a positive modulation feed current to the second peripheral solenoid 2 and a negative modulation feed current 1 to the central solenoid 0 establishes an electric field hotspot in pink zone c, in a first direction (appearing as an upward pointing vertical field vector on the viewing plane of FIG. 5B) along a pink zone first direction axis. Feeding opposite polarization feed currents, i.e., negative (−1) modulation feed current to the second peripheral solenoid 2 and positive modulation feed current to the zero solenoid 0 reverses the hotspot electric field direction. Line #15, expressed in terms of the SVEVM solenoid feed modulation state vector, {CM1, CM2, CM3, CM4, CM5, CM6, CM0} is {0, 1, 0, 0, 0, 0, −1}. Line #16 feeds solenoid feed current modulation state vector {0, −1, 0, 0, 0, 0, 1} to solenoids 1, 2, 3, 4, 5, 6, and 0. As can be seen from FIG. 4B line #13 and line #14, and line #17 though line 24, line #12, the above example establishment of a selectable direction electric field hotspot in pink zone c can likewise establish the hotspot electric field in any among the remaining pink zones e, g, i, k, and a.

Figures 6A, 6B:
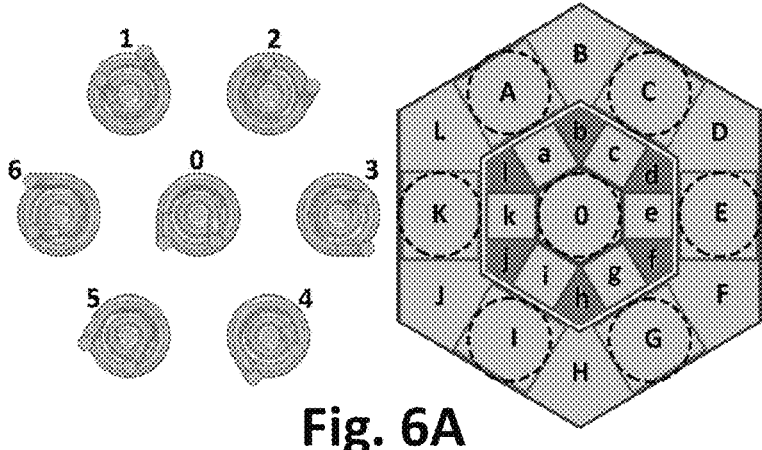
FIG. 6A shows the FIG. 2A solenoid location diagram, adjacent another highlighted version of the FIG. 2B zone map.
FIG. 6B shows an example table of solenoid current two-interval modulations for SVEVM time averaged placement, setting, and changing direction of time averaged electric field hotspots in the FIG. 6A zero zone.

FIG. 6A shows the FIG. 2A solenoid location diagram adjacent a zone map highlighting the "purple" zones. FIG. 6B shows a table of solenoid feed current modulations that can be applied to the purple zones' respective defining solenoids to establish desired hotpot electric field in said zones. The purple zones, continuing with the example solenoid and zone naming scheme, are zones b, d, f, h, j, and l. FIG. 5B shows an example table of six (6) different SVEVM solenoid modulation state vectors that can feed, e.g., via a controllable modulating current source, the zone-specific set of three solenoids associated with each purple zone. Each of the zone-specific sets of three solenoids includes an adjacent pair of peripheral solenoids and the central solenoid 0. Geometrically, each purple zone has a centroid that is centered on a line that extends in a radial direction away (or toward) the center of the central solenoid 0 and bisects a line segment connecting the centers of the two peripheral solenoids. For example, for purple zone, steps to locating the centroid can include defining a reference line segment that extends from the center of one among the two peripheral solenoids, i.e., the first peripheral solenoid 1 and the second peripheral solenoid and the second solenoid to the other of said two solenoids.

Referring to FIG. 6B, arbitrarily selected purple zone b will be used as a representative example. Establishing a TMS electric field in c, which is located on a midpoint between the central solenoid 0 and the second peripheral solenoid 2, and by said two solenoids, defined by the consecutive first peripheral solenoid 1 and second peripheral solenoid 2, line #15 and #16 show that feeding a positive modulation feed current to the second peripheral solenoid 2 and a negative modulation feed current 1 to the central solenoid 0 stablishes an electric field hotspot in pink zone c, in a first direction (appearing as an upward pointing vertical field vector on the plane of FIG. 6B) along a pink zone first direction axis, and feeding opposite polarization feed currents, i.e., feeding a reverse polarization, i.e., negative modulation feed current to the second peripheral solenoid 2 and positive modulation feed current to the zero solenoid 0 reverses the hotspot electric field direction. Expressed in terms of the SVEVM solenoid feed modulation state vector, {CM1, CM2, CM3, CM4, CM5, CM6, CM0}, line #15 feeds {0, 1, 0, 0, 0, 0, −1} and line #16 feeds {0, −1, 0, 0, 0, 0, 1} to solenoids 1, 2, 3, 4, 5, 6, and 0. As can be seen from FIG. 6B line #13 and line #14, and line #17 though line 24, line #12, the above example establishment of a selectable direction electric field hotspot in pink zone c can likewise establish the hotspot electric field in any of the remaining pink zone e, g, i, k, or a.

Above-described embodiments are described with reference to example that establish TMS hotspot E-fields within one zone. According to various embodiments, TMS hotspot E-fields can be generated to span contiguous zones.

Figure 7:
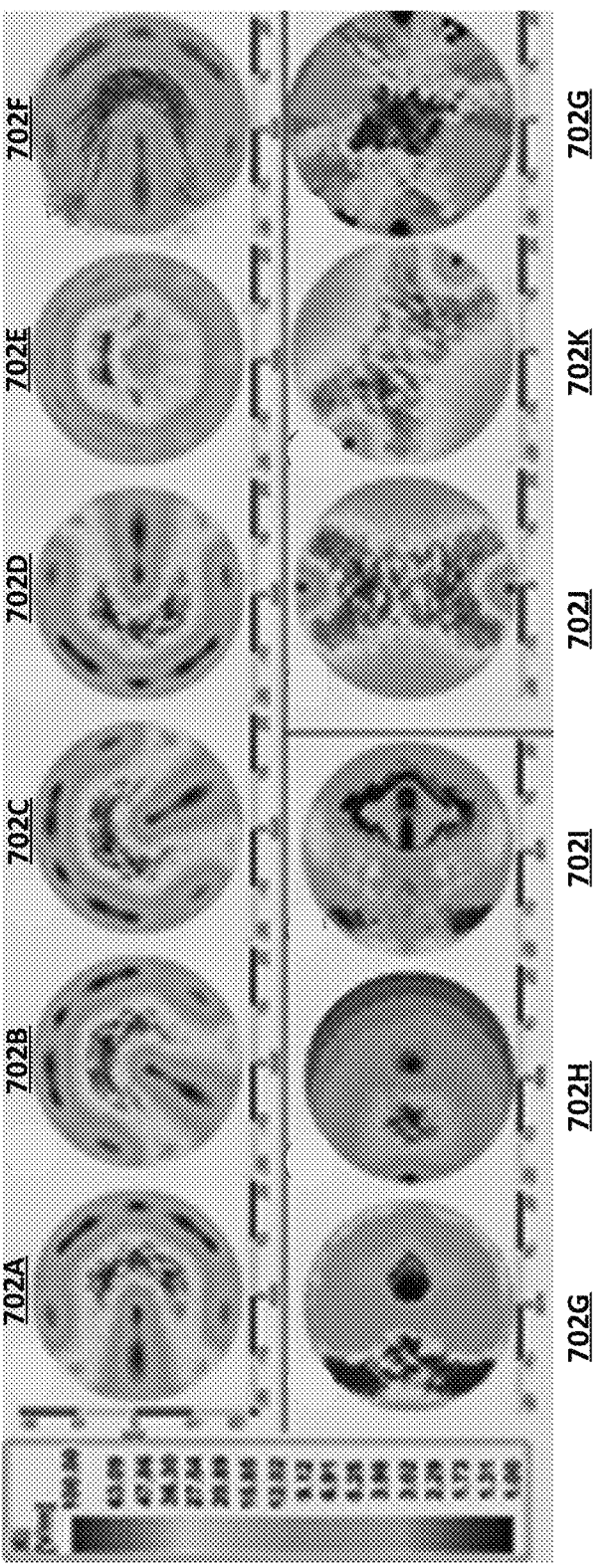
FIG. 7 shows example multi-zone electric field hotspots established by time averaged feeding of successive sub-interval duration SVEVM solenoid current modulation state vectors.

FIG. 7 fields 702g through 702i shows that different patterns of time-averaged destructive interference can be obtained. Field 702g shows a bow-shape pattern of E-field magnitude with the polarization of coils 0, 2, 3, 4, and 5 with 2.76 kA (same phase). Field 702h shows the magnitudes for the stimulation of the pink zone "k" with E-field vectors in the opposite direction (upwards) to those of the field 702g (downwards). This is obtained with 5 kA and −5 kA in coils 6 and 0, respectively. The result is similar to the bow-shape pattern, but with the E-field in zone "k" significantly attenuated. The configuration can be particularly useful for simultaneous stimulation of symmetrical targets in the left and right lobes of the rat brain. The pattern in field 702j was obtained polarizing coils 1 and 5 with 5 kA and 2 and 4 with −5 kA. The same pattern rotated 60° was also obtained, as shown in field 70k. The averaged result is shown in FIG. 41, stimulating the zone "0" below the central coil.

Blue zones, which align with the peripheral solenoids 1, 2, 3, 4, 5, and 6, can require additional structure to achieve close alignment. One configuration can be a shadow set of peripheral coils, providing peripheral coil pairs, as opposed to the above-described single peripheral coils. Current feed can comprise a two-step feed to the central solenoid, and a consecutive two of the paired peripheral solenoid.

Figures 8A, 8B:
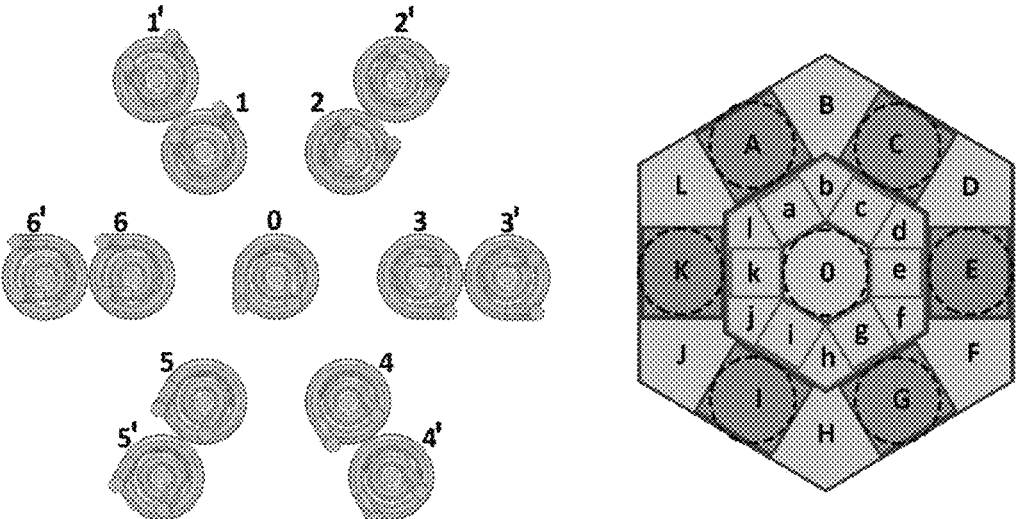
FIG. 8A shows an example "paired" peripheral coil arrangement generally according to the FIG. 2A extraction of the FIG. 1A. arrangement, adjacent a highlighted "blue" or peripheral solenoid version of the FIG. 2B zone mapping.
FIG. 8B shows an example table of solenoid current two-interval modulations for SVEVM time averaged placement, and setting and changing direction of time averaged electric field hotspots in the FIG. 7A example blue or peripheral zones

FIG. 8A shows an example "paired" peripheral coil arrangement adjacent a highlighted "blue" or peripheral solenoid version of the FIG. 2B zone mapping. FIG. 8B shows an example table of solenoid current two-interval modulations for SVEVM time averaged placement and setting and changing direction of time averaged electric field hotspots in the FIG. 8A example blue or peripheral zones. The FIG. 8A example blue zones are labeled Methods according to other embodiments provide, among other features, a novel and substantial constraining of a particular performance reducing spreading of magnetic flux lines passing through neural tissue under a coil. The performance reducing spreading is caused by the electrical charges that the flux lines are intended to induce. The spreading can significantly compromise focality of TMS stimulation. Solving it has been a technical problem, though, because as stated above it is caused by the charges that the flux lines are intended to induce. Substantive causes of the spreading include spreading of electrical charges induced by the flux lines, outward from their intended depth direction flow path toward the target region, due both to the charges being of like sign, and charge migration and dispersion inherent to such charges having a higher charge density than surrounding regions.

In systems and methods according to various embodiments, novel features and combinations include providing mutually repelling forces, which act against migration and dispersion inherent to such charges having a higher charge density than surrounding regions. Eventually, after certain depth, the dispersion of the peripheral charges allows the central charges to spread out. However, the restriction will provide the central charges the chance to reach the target in a still relatively compact group, with an associated high current density. In this way, the quintuple coil confines the path of the central group of induced charges to point and pass through the target point, increasing the E-field on it. For purposes of description the technique will be referred to as "oriented control of the electric field based on the directional vector of highest current density." On the other hand, the propagation of peripheral charges will occur outwards in a dispersive manner, which will form a conical pattern to be called "peripheral path of highest current density." This path, though unoriented, is still necessary to provide control over the central path.

Systems and methods according to various embodiment: provide these features through novel spatial configuration of coils and their respective structure, in combination with a particular configuration of generating and feeding coil currents. The spatial configuration can include a central coil surrounded by a particular population and arrangement of peripheral coils. Configurations of current feeds can include a central coil feed current causing the central coil to generate central coil magnetic flux lines inducing the above-described central region charge flow, and can include peripheral coil feed currents causing each peripheral coil to induce a corresponding peripheral region charge flow of like-sign charges of the same sign as, and in phase with, the central region charge flow.

According to various embodiments, configuration of the coils, e.g., population and arrangement of the peripheral coils relative to one another and to the central coil, and configuration of individual coil cores and winding structures, and configuration of coil feed currents, can be set such that the peripheral region charge flows exert combined repelling forces on the central charge flow that substantially constrain central charge spreading and keep the central charge flow aligned with and constrained with high focality to its longitudinal axis, at least until the flow passes through the target region. The constraint of spreading therefore provides a path of increased current density along the central axis, raising the associated E-field in the target region.

Figure 9A:
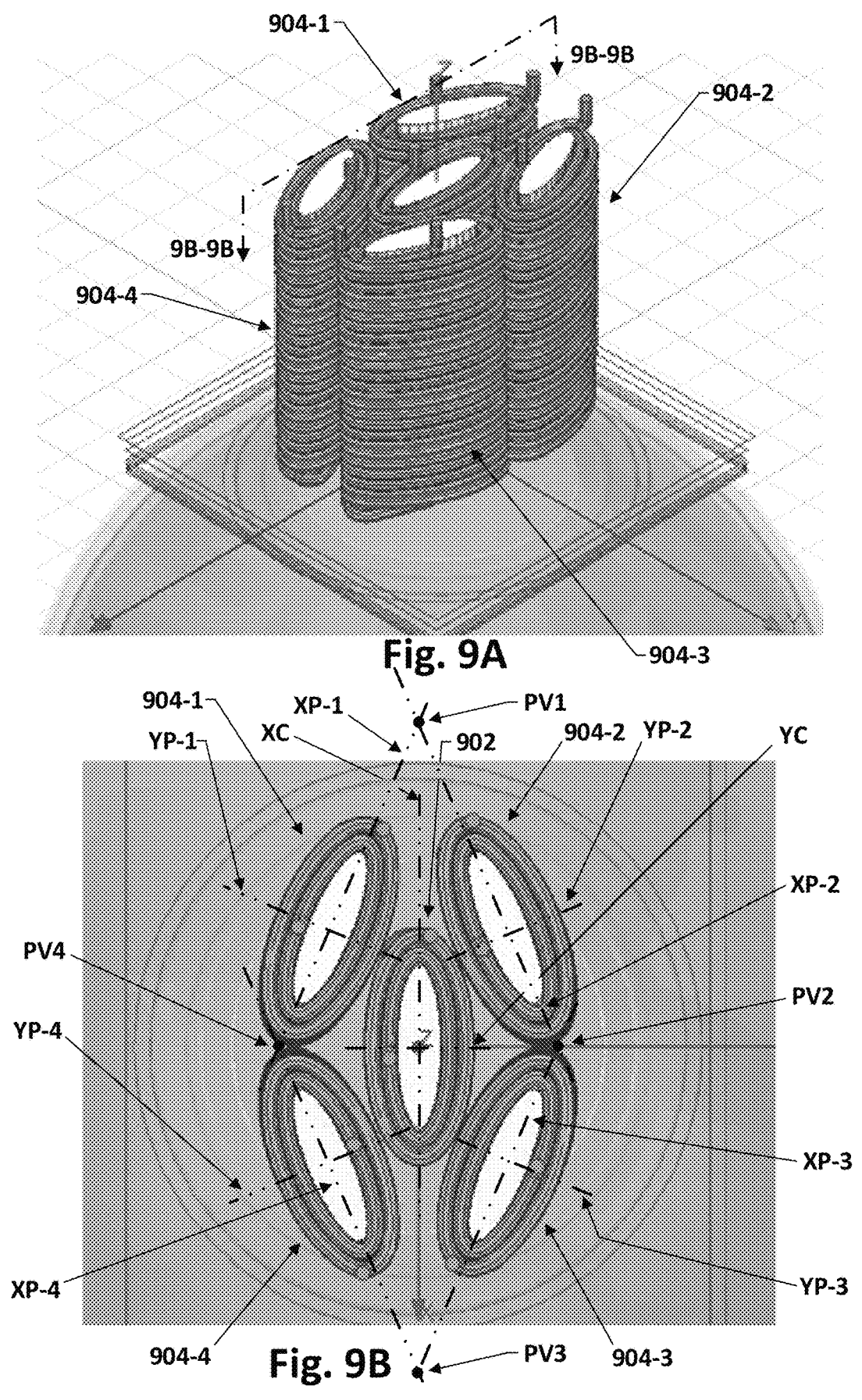

FIG. 9A shows a perspective view of an example quintuple solenoid arrangement 900, hereinafter "arrangement 900," for multi-solenoid high focality TMS systems and methods in accordance with one or more embodiments. FIG. 9B shows a top projection view of example structures of the FIG. 9A arrangement 900, quintuple solenoid arrangement, viewed from the FIG. 9A projection 9B-9B. Referring to FIG. 9B, arrangement 900 includes a central solenoid 902, a first peripheral solenoid 904A, second peripheral solenoid 904B, third peripheral solenoid 904C, and fourth peripheral solenoid 904D. For purposes of description, the first, second, third, and fourth solenoids will be collectively referenced as "peripheral solenoids 904" and generically referenced, in the singular sense, as "peripheral solenoid 904."

The FIGS. 9A and 9B example central solenoid 902 is shown as a dual winding elliptical solenoid having an elliptical core and wrapped around the elliptical core, a dual winding. The dual winding includes an inner winding and an outer winding. The ellipse of the central solenoid has major axis XC and minor axis YC. The central solenoid 902 has an outer width aligned with the minor axis YC, and an outer length aligned with the major axis XC.

The FIGS. 9A and 9B example peripheral solenoids 904 are shown as dual winding elliptical solenoids having an elliptical core and wrapped around the elliptical core a dual winding that includes an inner winding and an outer winding. The ellipse of the first peripheral solenoid 904-1 has major axis XP-1 and minor axis YP-1; the ellipse of the second peripheral solenoid 904-2 has major axis XP-2 and minor axis YP-2-1; the ellipse of the third peripheral solenoid 904-3 has major axis XP-3, and minor axis YP-3; and the ellipse of the fourth peripheral solenoid has major axis XP-4, and minor axis YP-4. Each peripheral solenoid 904 has an outer width aligned with its minor axis and an outer length aligned with its major axis. For purposes of description, it will be assumed that the peripheral solenoids 904 are identically structured. This is only an example and not a limitation on practices in accordance with disclosed embodiments the appended claims. Identical structure can be, for example, as represented by the FIG. 9B example structure of the first peripheral solenoid 904-1. The example peripheral solenoid structure includes an elliptical core and wrapped around the elliptical core a dual winding that includes an inner winding and an outer winding.

According to various embodiments, each peripheral solenoid 904 can be arranged such that one of its two opposite outer width surfaces contacts an outer surface of the central solenoid 902, and the four peripheral solenoids 904 can be further arranged such that the major axis XP1 of the first peripheral solenoid 904-1 and the major axis XP3 of the third peripheral solenoid 904-3 extend mutually parallel, the major axis XP2 of the second peripheral solenoid 904-2 and the major axis XP4 of the fourth peripheral solenoid 904-4 extend mutually parallel, XP1 and XP3 form two mutually opposite sides of a reference parallelogram, and XP2 and XP4 form two other opposite mutually parallel sides of the reference parallelogram. For convenient reference in FIG. 9B, the respective vertices of the example reference parallelogram are labeled PV1, PV2, PV3, and PV4.

FIG. 10A shows an annotated front projection of an operation of the central solenoid, aligned above a target region, and corresponding dispersion and migration of induced charges, assuming removal, for purposes of illustration, of peripheral electric fields in accordance various embodiments; FIG. 10B shows paths of peripheral solenoid induced nucleation. FIG. 10C shows confinement of the central solenoid induced charges by the peripheral solenoid charges, in a process of oriented control of the electric field based on the directional vector of highest current density in accordance with various embodiments.

As seen from FIG. 10A, there is dispersion and migration of the charges induced by the central solenoid coil, to zones of lower charge densities. A solution is provided in accordance with one or more embodiments, by the quadruple arrangement of peripheral solenoids, shown in FIG. 10B, which generate a respective four nuclei of induced charges in the surroundings. The projection view of FIG. 10B renders only two of the four nuclei visible. Being of the same sign as the charges induced by the central solenoid coil, the induced peripheral charges repel the charges induced by the former. The propagation of peripheral charges will occur outwards in a dispersive manner, which will form a conical pattern to be called "peripheral path of highest current density." This path, though unoriented, provides through methods in accordance with this embodiment control over the central path.

The result visible in FIG. 10C, is that the charges induced by the central solenoid are forced to propagate vertically along the z-axis, which is an example of the above-described "oriented central path of highest current density."

Embodiments of the disclosure provide a customized array of five dual-winding solenoids, each of which includes a ferromagnetic core, to restrict the stimulation to areas as small as, for example, 1 mm$^2$. In a non-limiting example for purposes of illustration, each solenoid was a double winding, made with 50 turns, 25 turns for the inner winding and 25 turns for the outer winding, of a wire with thickness of 1 mm, height of 25.4 mm, and elliptical top-view cross section of semi-major axis of 10.6 mm, and semi-minor axis of 2.8 mm. The ferromagnetic cores were V-shape tip sharpening and formed of AISI 1010 carbon steel of 2 T of saturation flux density (Bsat) at 4×104 A/m. The initial relative permeability μr of the magnetic core material was 667.75. The cores have the same top-view cross section as the coils, with minimal clearance just to make it fit inside the winding. The centroids of each solenoid in the example were placed forming a reference quadrilateral or parallelogram of sides 10.6 mm×7.95 mm. The above example dimensions, e.g., semi-major axis of 10.6 mm, semi-minor axis of 2.8 mm, wire thickness of 1 mm, or height of 25.4 mm, the example quadrilateral sides of the parallelogram, or dimensions of the coil, the example characteristics, e.g., ferromagnetic cores being V-cross section of the wire, or example quantities, e.g., number of turns, or parameter values, e.g., saturation flux density, are non-limiting examples are not to be understood as any limitation on practices in accordance with disclosed embodiments or the appended claims. Persons of ordinary skill, upon reading this disclosure in its entirety, can readily implement methods and systems in accordance with disclosed embodiments and the appended claims that can use one or more variations, adaptations, modifications, and substitutions for the examples. For example, and without limitation, the AISI 1010 carbon steel ferromagnetic material of the core or the winding is only an example. It is not intended as a statement of preference or as a limitation on practices in accordance with disclosed embodiments. The AISI 1010 carbon steel can be replaced with another material of similar or better electromagnetic or mechanical properties.

Figures 11A, 11B, 11C:
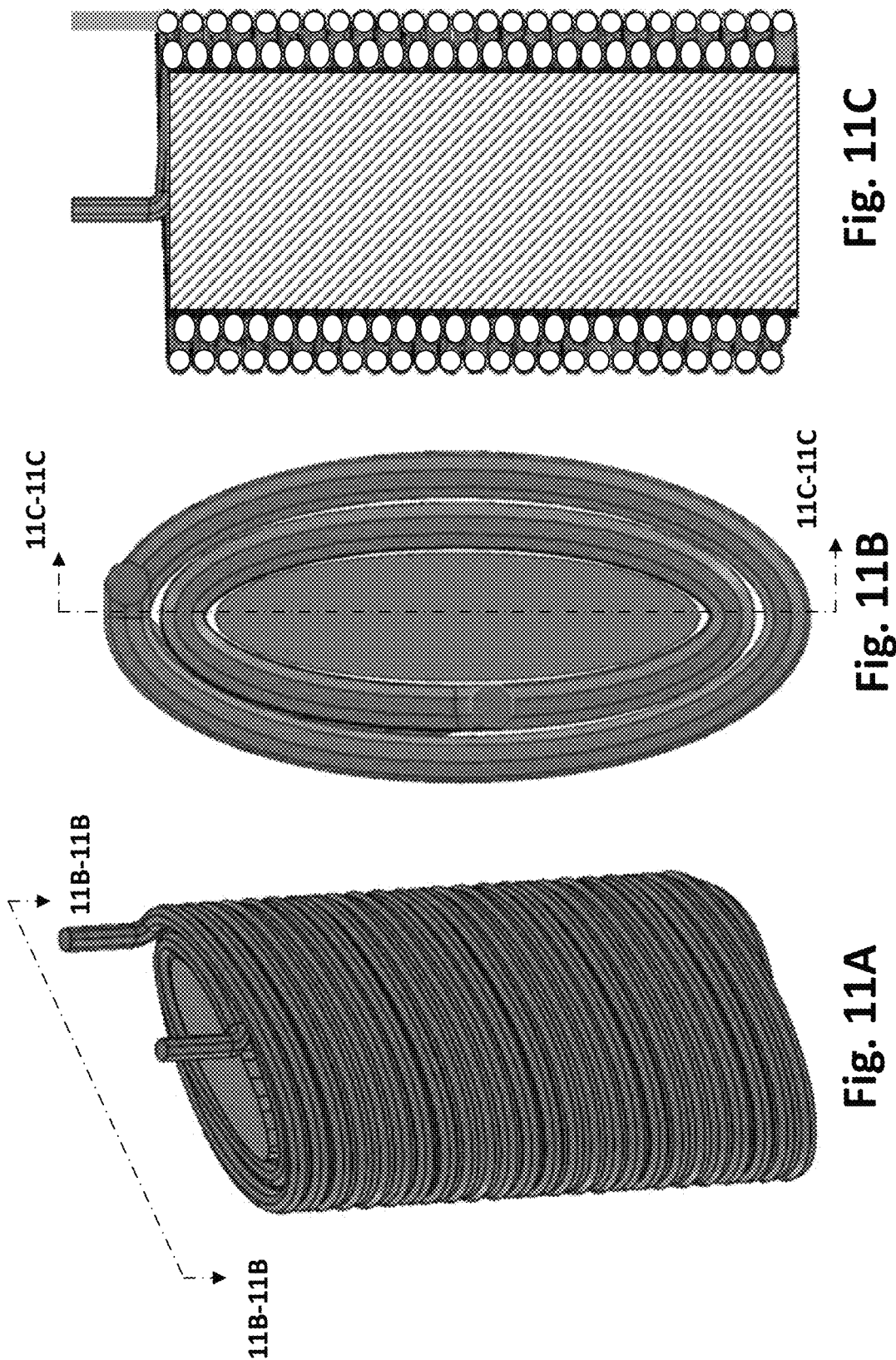
FIG. 11A shows a perspective view of one an example elliptical dual wound solenoid.
FIG. 11B a top of the FIG. 11A elliptical dual wound solenoid, from projection 11B-1B.
FIG. 11C shows a cross-section of the example dual-would elliptical solenoid, from FIG. 11B projection 11C-11C.

FIG. 11A shows a perspective view of one example elliptical dual wound solenoid; FIG. 11B a top view of the FIG. 11A elliptical dual wound solenoid, from projection 11B-11B; and FIG. 11C shows a cross-section of the example dual-would elliptical solenoid, from FIG. 11B projection 11C-11C.

The ferromagnetic material of the core or the winding is not a limitation, and may be replaced with a material of similar or better electromagnetic or mechanical properties. The same applies for minor details such as cross section of the wire, final dimensions of the coil, shape of the cross section, separation between solenoids, orientation of the solenoids or any other physical characteristic always that the reasonable criterion may be applied to ensure that minimally modified versions of the coil are within the scope of this disclosure.

Figure 12:
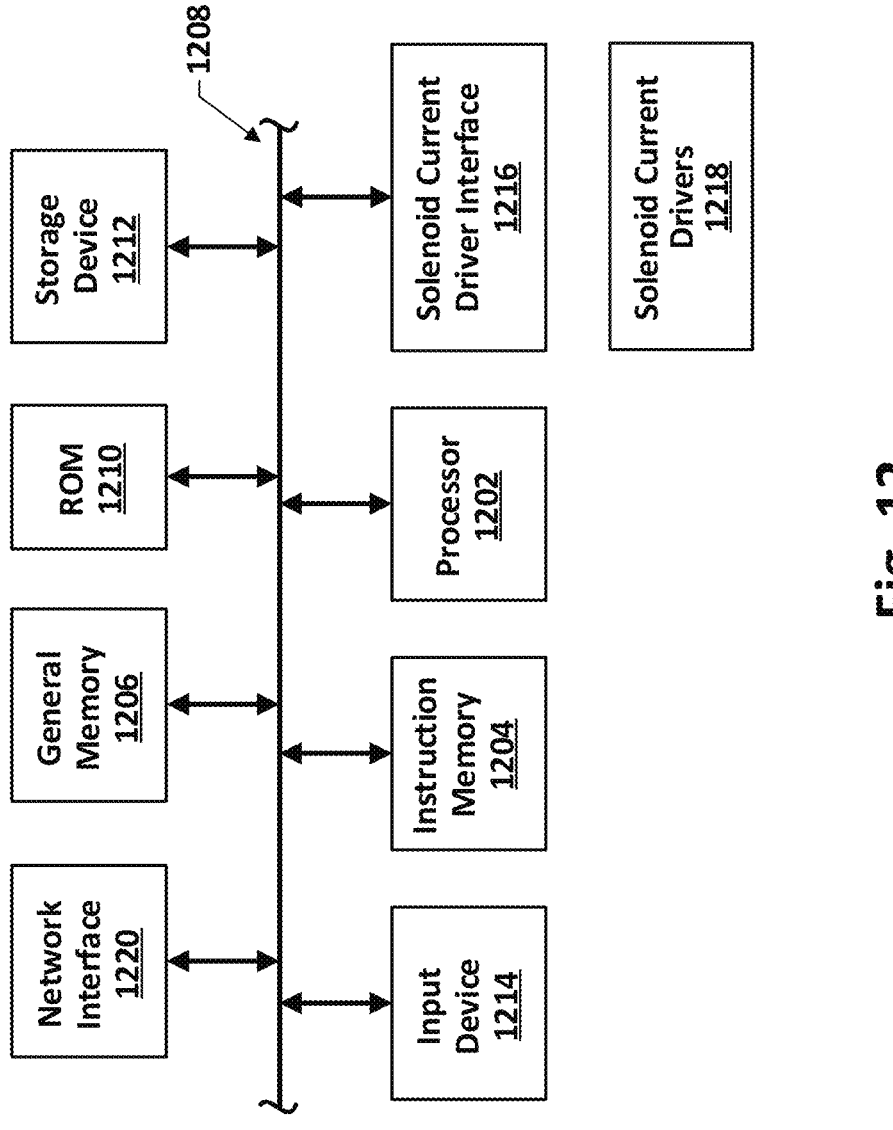
FIG. 12 shows a functional block schematic of an example processor device for practices of computer implemented processes in accordance with the present disclosure.

FIG. 12 shows a functional block schematic of an example processor device 1200 for practices of computer implemented processes in accordance with the present disclosure. The device 1200 may include a processor 1202, coupled to an instruction memory 1202 and a general memory 1206 by a bus 1208. The bus 1208 may also couple to a read only memory (ROM) 1210, a storage device 1212, and an input device 1214. The bus 1208 may couple to a solenoid current driver interface 1216 that may in turn feed current control signals or commands to solenoid current drivers 1218. The device 1200 may include a communication or network interface 1220 that can couple to the bus 1208.

Processor 1202 may include one or more processors, e.g., microprocessors that may execute stored native instructions associated with the one or more processes. Processor 1202 may be implemented by, for example, reduced instruction set (RISC) or complex instruction step (CISC) sequencing logic, which can include, for example, one or among programmable logic such as Field Programmable Gate Arrays (FPGAs), Graphic Processing Units (GPUs), and accelerators. Processor 1202 may include software, hardware, or a combination of software and hardware for executing processes described herein. The general memory 1206 may include a random-access memory (RAM) that can store instructions for execution by processor 1202. The ROM

1210 may include a static storage device, such as an Electrically Erasable Programmable ROM (EEPROM). Storage device 1212 may include a magnetic, optical, and/or solid state (e.g., flash drive) recording medium and its corresponding drive. General memory 1206, ROM 1210 and storage device 1212 may each be referred to herein as a "non-transitory computer-readable medium" or a "non-transitory storage medium." The processes/methods set forth herein (or at least a portion of the processes/methods set forth herein) can be implemented as instructions, which can be logically arranged as logic modules stored in the instruction memory 1204, the ROM 1210, or storage device 1212, or combinations thereof. An input device 1214 may include, for example, keyboard, a display with a touch sensitive panel.

Device 1200 may perform certain operations or processes, as may be described herein. Device 1200 may perform these operations in response to processor 1202 executing software instructions contained in a computer-readable medium, such as instruction memory 1204.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be separated from or combined with the features of any of the other of the several embodiments without departing from the scope or spirit of the present invention. Any recited method can be carried out in the order of events recited or in any other order that is logically possible.

While the invention has been described herein in connection with exemplary embodiments and features, one skilled in the art will recognize that the invention is not limited by the disclosure and that various changes and modifications may be made without departing from the scope of the invention as defined by the appended claims.

What is claimed is:

1. A method for establishing a selectively focusable and steerable electric field within a transcranial region, comprising positioning, above the transcranial region, an arrangement of solenoids;

selectively establishing, in response to a zone selection data, a target zone, selectable from among a plurality of zones;

identifying, based on the target zone, a zone-specific set of Q solenoids, Q being a positive integer greater than one, that are from among the arrangement of solenoids, wherein the zone-specific set of Q solenoids includes at least one pair of mutually adjacent ones of the solenoids in the arrangement of solenoids; and establishing a transcranial magnetic stimulation (TMS) inducing time-varying magnetic field, configured to induce a target hotspot TMS electric field, which is focalized to the target zone, by steps comprising:

generating a Q-element solenoid feed modulation state vector that defines a Q-current element feed current modulation state that is configured to cause the zone-specific set of Q solenoids to generate Q individual, spatially configured, time-varying magnetic fields that, in combination, are sufficient to establish the TMS inducing time-varying magnetic field, configured to induce the target hotspot TMS electric field, which is focalized to the target zone, and feeding Q individually modulated solenoid feed currents, at respective modulation states in accordance with the Q-current element feed current modulation state, to the zone-specific set of Q solenoids.

2. The method of claim 1, wherein the arrangement of solenoids includes a misaligned array of solenoids, comprising:

a middle row of solenoids, centered at respective middle row solenoid positions spaced apart from one another by a center-to-center spacing along a middle row axis, an upper row of solenoids, centered at respective upper row solenoid positions spaced from another by the center-to-center spacing along an upper row axis that extends parallel to the middle row axis, the upper row solenoid offset from the middle row solenoid positions by one-half the center-to-center spacing; and a lower row of solenoids, centered at respective lower row solenoid positions spaced from another by the center-to-center spacing along a lower row axis that extends parallel to the middle row axis, the upper row solenoid offset from the middle row solenoid positions by one-half the center-to-center spacing.

3. The method of claim 2, wherein the zone selection data further includes a target direction data and generating the Q-element solenoid feed modulation state vector is based at least in part on the target direction data; and wherein the method further comprises:

receiving an updated target direction data, and generating, based at least in part on the updated target direction data, an updated Q-element solenoid feed modulation state vector, configured to define an updated Q-current element feed current modulation state, which is configured to cause the zone-specific set of Q solenoids to generate updated Q individual, spatially configured, time-varying magnetic fields that, in combination, update the TMS inducing time-varying magnetic field to induce an updated target hotspot TMS electric field in an updated direction.

4. The method of claim 1, wherein:

the arrangement of solenoids comprises a central solenoid at a reference location on a reference plane, and a plurality of peripheral solenoids at respective peripheral locations that are on the reference plane and radially spaced from the reference location, and the plurality of zones comprises a plurality of inter-solenoid zones, and the plurality of inter-solenoid zones comprises a plurality of first inner inter-solenoid zones, and a plurality of second inner inter-solenoid zones, wherein:

for each of the first inner inter-solenoid zones, the corresponding zone-specific set of solenoids comprises the central solenoid and a corresponding different pair of the peripheral solenoids; and for each of the second inner inter-solenoid zones, the corresponding zone-specific set of solenoids comprises the central solenoid and a corresponding one of the peripheral solenoids.

5. The method of claim 4, wherein:

the plurality of peripheral solenoids includes six peripheral solenoids, each at a respective one among six peripheral locations, spaced equally about a reference circle centered at the central solenoid, and the plurality of second inner inter-solenoid zones includes six second inner inter-solenoid zones, each having a centroid aligned on a reference line segment that extends from the central location to the peripheral location of the one of the peripheral solenoids.

6. The method of claim 5, wherein each of the second inner-solenoid zones has a geometry corresponding to a rectangle having one side tangential to the central solenoid and another side, opposite the one side, tangential to the one of the six peripheral solenoids.

7. The method of claim 5, wherein:

the target hotspot TMS electric field is established as a first inner inter-solenoid zone electric field, aligned with a selectable one of the first inner inter-solenoid zones, and has a target spatial configuration, the Q-element solenoid feed modulation state vector is configured to define the Q-current element feed current modulation state in a manner that causes to the central solenoid and the pair of peripheral solenoids within the zone-specific set of Q solenoids to generate a corresponding time varying, spatially configured central magnetic field, and to generate a corresponding pair of peripheral time-varying, spatially configured magnetic fields that, in combination with the time varying, spatially configured central magnetic field, establish the target hotspot TMS electric field within the one first inner inter-solenoid zone.

8. The method of claim 7, wherein:

selectively establishing the first inner inter-solenoid zone electric field includes establishing the first inner inter-solenoid electric field with a particular first inner inter-solenoid zone electric field direction among a plurality of different first inner inter-solenoid zone electric field directions, which include a first inner inter-solenoid zone electric field first direction and a first inner inter-solenoid zone electric field second direction, which is opposite the first inner inter-solenoid zone electric field first direction, the Q-element solenoid feed modulation state vector is configured to define the Q-current element feed current modulation state, for the first inner inter-solenoid zone electric field first direction, to feed the pair of peripheral solenoids respective current pulses of a positive phase, and to feed the central solenoid with respective current pulses of a negative phase, and the Q-element solenoid feed modulation state vector is configured to define the Q-current element feed current modulation state, for the first inner inter-solenoid zone electric field second direction, to feed the pair of peripheral solenoids respective current pulses of the negative phase, and to feed the central solenoid with respective current pulses of the positive phase.

9. The method of claim 5, wherein:

the target hotspot TMS electric field is a second inner inter-solenoid zone electric field, aligned with a selectable one of the second inner inter-solenoid zones, comprising:

the Q-element solenoid feed modulation state vector is configured to define the Q-current element feed current modulation state to cause the central solenoid to generate a corresponding time varying, spatially configured central magnetic field, and to cause the one peripheral solenoid to generate a corresponding peripheral time-varying, spatially configured magnetic field that, in combination with the time varying, spatially configured central magnetic field, establishes the second inner inter-solenoid zone electric field with the target hotspot TMS electric field.

10. The method of claim 9, wherein:

selectively establishing the second inner inter-solenoid zone electric field includes establishing the second inner inter-solenoid electric field with a particular second inner inter-solenoid zone electric field direction among a plurality of different second inner inter-solenoid zone electric field directions, which include a second inner inter-solenoid zone electric field first direction and a second inner inter-solenoid zone electric field second direction, which is opposite the second inner inter-solenoid zone electric field first direction, comprising the Q-element solenoid feed modulation state vector:

defining, for the second inner inter-solenoid zone electric field first direction, the Q-current element feed current modulation state to feed the one peripheral solenoid respective current pulses of a positive phase, and to feed the central solenoid with respective current pulses of a negative phase, and defining, for the second inner inter-solenoid zone electric field second direction, the Q-current element feed current modulation state to feed the one peripheral solenoid respective current pulses of the negative phase, and to feed the central solenoid with respective current pulses of the positive phase.

11. The method of claim 5, wherein:

the plurality of inter-solenoid zones further comprises six outer inter-solenoid zones;

for each of the outer inter-solenoid zones, the corresponding zone-specific set of Q solenoids comprises a corresponding different pair of the peripheral solenoids; and each outer inter-solenoid zone has a centroid aligned on a reference line segment that extends from the peripheral location of one of the peripheral solenoids forming the pair of the peripheral solenoids, and the peripheral location of the other peripheral solenoids forming the pair of the peripheral solenoids.

12. The method of claim 11, wherein:

the target hotspot TMS electric field is an outer inter-solenoid zone electric field, aligned with a selectable one of the six outer inter-solenoid regions, the Q-element solenoid feed modulation state vector is configured to define the Q-current element feed current modulation state to cause the central solenoid to generate a corresponding time varying, spatially configured central magnetic field, by feeding the current pulses to the pair of the peripheral solenoids corresponding to the one of the six outer inter-solenoid regions, with a modulation state causing the pair of peripheral solenoids to generate a corresponding pair of peripheral time-varying, spatially configured magnetic fields that, in combination, establish the target hotspot TMS electric field as the outer inter-solenoid zone electric field.

13. The method of claim 12, wherein:

selectively establishing the outer inter-solenoid zone electric field includes establishing the outer inter-solenoid electric field with a particular outer inter-solenoid zone electric field direction among a plurality of different outer inter-solenoid zone electric field directions, which include an outer inter-solenoid zone electric field first direction and an outer inter-solenoid zone electric field second direction, which is opposite the outer inter-solenoid zone electric field first direction, and establishing the outer inter-solenoid electric field with the particular outer inter-solenoid zone electric field direction among the plurality of different outer inter-solenoid zone electric field directions comprises:

for the outer inter-solenoid zone electric field first direction, generating the Q-element solenoid feed modulation state vector with a configuration that defines the Q-current element feed current modulation state to feed one of the peripheral solenoids within the pair of peripheral solenoids respective current pulses of a positive phase, and to feed the other of the peripheral solenoids within the pair of peripheral solenoids with respective current pulses of a negative phase, and for the outer inter-solenoid zone electric field second direction, feeding the one peripheral solenoid within the pair of peripheral solenoids respective current pulses of the negative phase, and feeding the other peripheral solenoid within the pair of peripheral solenoids with respective current pulses of the positive phase.

14. The method of claim 1, wherein the arrangement of solenoids includes six peripheral solenoids, each at a respective one among six peripheral locations, spaced equally about a reference circle centered at the central solenoid; and the target zone is selectable among the plurality of zones and a central zone, the central zone being aligned with the central solenoid, and the method further comprises selectively establishing the target hotspot TMS electric field as a central zone TMS electric field, aligned with the central zone, by operations including:

generating the Q-element solenoid feed modulation state vector to define the Q-current element feed current modulation state to cause the central solenoid to generate a corresponding time-varying, spatially configured central magnetic field, and feeding each of the six peripheral solenoids a modulated sequence having two sub-intervals and comprising during the first sub-interval a first modulation and, during the second sub-interval, a second modulation, the first modulation and the second modulation each being between a positive phase ON state, a negative phase ON state, and OFF state, wherein the first modulation is configured to cause the six peripheral solenoids to generate, in combination, a first interval combination time-varying, spatially configured magnetic field, and the second modulation is configured to cause the six peripheral solenoids to generate, in combination, a second interval combination time-varying, spatially configured magnetic field, configured to average, over the interval, to an averaged combination time-varying magnetic field that establishes the target hotspot TMS electric field in the central zone.

15. The method of claim 14, wherein the six peripheral solenoids comprise a first peripheral solenoid, a second peripheral solenoid, a third peripheral solenoid, a fourth peripheral solenoid, a fifth peripheral solenoid, and a sixth peripheral solenoid, establishing the target hotspot TMS electric field in the central zone includes selectively setting a direction of the target hotspot TMS electric field among a plurality of different central zone hotspot TMS electric field directions, including a central zone hotspot TMS electric field first direction and a central zone hotspot TMS electric field second direction, which is rotated 60 degrees from the central zone hotspot TMS electric field first direction, and setting the direction of the central zone hotspot TMS electric field at the central zone TMS electric field first direction includes generating the Q-element solenoid feed modulation state vector at a first direction configuration of the first modulation and a first direction configuration of the second modulation, the first direction configuration of the first modulation comprises:

an ON positive phase current pulse to the first peripheral solenoid, an ON negative phase current pulse to the second peripheral solenoid, an OFF current pulse to the third peripheral solenoid, an ON negative phase current pulse to the fourth peripheral solenoid, an ON positive phase current pulse to the fifth peripheral solenoid, and an OFF current pulse to the sixth peripheral solenoid, and the first direction configuration of the second modulation comprises:

an OFF current pulse to the first peripheral solenoid, an ON positive phase current pulse to the second peripheral solenoid, an ON negative phase current pulse to the third peripheral solenoid, an OFF current pulse to the fourth peripheral solenoid, an ON negative phase current pulse to the fifth peripheral solenoid, and an ON positive phase current pulse to the sixth peripheral solenoid; and setting the direction of the central zone hotspot TMS electric field and the central zone hotspot TMS electric field second direction includes setting a second direction configuration of the first modulation and a second direction configuration of the second modulation, wherein:

the second direction configuration of the first modulation comprises:

an OFF current pulse to the first peripheral solenoid, an ON positive phase current pulse to the second peripheral solenoid, an ON negative phase current pulse to the third peripheral solenoid, an OFF current pulse to the fourth peripheral solenoid, an ON negative phase current pulse to the fifth peripheral solenoid, an ON positive phase current pulse to the sixth peripheral solenoid, and the second direction configuration of the second modulation comprises:

an ON positive phase current pulse to the first peripheral solenoid, an OFF current pulse to the second peripheral solenoid, an ON positive phase current pulse to the third peripheral solenoid, an ON negative phase pulse to the fourth peripheral solenoid, an OFF current pulse to the fifth peripheral solenoid, and an ON negative phase current pulse to the sixth peripheral solenoid.

16. A method for establishing and actively constraining for at least a target region depth a moving electrical charge flow through a biological tissue, along a flow path that extends in a depth direction aligned with a target region that is spaced from a surface of the biological tissue in the depth direction, comprising:

positioning, an arrangement of solenoids above an area of the biological tissue that includes the target region, wherein:

the arrangement of solenoids comprises a central solenoid located at a reference location on a reference plane, and a plurality of peripheral solenoids located at respective peripheral locations that are on the reference plane and radially spaced from the reference location, and the positioning the arrangement of solenoids includes aligning the central solenoid with the target region; and inducing, via the arrangement of solenoids, central region electrical charges in the biological tissue, within a central region of the biological tissue, which is spaced above and aligned with the target region; and urging the central region electrical charges into a central electrical charge flow, having a mean aligned and parallel to the flow path, wherein:

inducing, via the arrangement of solenoids, central region electrical charges in the biological tissue comprises steps including:

applying to the central region the biological tissue a central electrical field of electrical charge inducing magnitude, by operations including feeding each of the central solenoid and the plurality of peripheral solenoids respective modulated feed currents configured to:

cause the central solenoid to generate a corresponding time-varying, spatially configured central magnetic field, and cause the peripheral solenoids to generate, in combination, respective time-varying, spatially configured peripheral magnetic fields, wherein the time-varying, spatially configured central magnetic field magnetic field, in combination with the time-varying, spatially configured peripheral magnetic fields average, over a time interval, to the central electrical field of electrical charge inducing magnitude, and feeding the peripheral solenoids respective modulated feed currents is configured such that configured to establish a plurality of repulsive forces, each of the repulsive forces being configured to urge against the central region electrical charges in the central region electrical charge flow, each of the repulsive forces being in a direction inward from a respective peripheral location, toward and normal to the flow path.

17. The method of claim 16, wherein:

the peripheral locations comprise a plurality of peripheral locations, each spaced radially from the flow path, and the plurality of peripheral locations includes a first peripheral location, a second peripheral location, a third peripheral location, and a fourth peripheral location.

18. The method of claim 17, wherein feeding the peripheral solenoids respective modulated feed currents is further configured such that establishing the plurality of repulsive forces comprises:

inducing first peripheral region electrical charges at the first peripheral location, inducing second peripheral region electrical charges at the second peripheral location, inducing third peripheral electrical charges at the third peripheral location, and inducing fourth peripheral electrical charges at the fourth peripheral location;

urging the first peripheral region electrical charges toward a first peripheral path electrical charge flow;

urging the second peripheral region electrical charges toward a second peripheral path electrical charge flow;

urging the third peripheral region electrical charges toward a third peripheral path electrical charge flow; and urging the fourth peripheral region electrical charges toward a fourth peripheral path electrical charge flow, wherein the first peripheral path electrical charge flow, the second peripheral path electrical charge flow, the third peripheral path electrical charge flow, and the fourth peripheral path electrical charge each initiate parallel to the depth direction and to the flow path direction of the central electrical path charge flow.

19. The method of claim 16, wherein the plurality of repulsive forces includes a first peripheral repulsive force, a second peripheral repulsive force, a third peripheral repulsive force, and a fourth peripheral repulsive force.

20. The method of claim 19, wherein:

applying the central electrical field of electrical charge inducing magnitude comprises passing a central coil current through a central coil that is above and aligned at a central location that is aligned with the target region; and establishing the plurality of repulsive forces includes applying at each of a plurality of peripheral locations a respective peripheral electrical field of electrical charge inducing magnitude, in turn establishing a corresponding plurality of peripheral location electrical charge flows, each of the peripheral location electrical charge flows being of the same sign as the central region electrical charge flow.

* * * * *